US005693514A

United States Patent [19]
Dorian et al.

[11] Patent Number: 5,693,514
[45] Date of Patent: Dec. 2, 1997

[54] NON-FIBROGENIC HIGH MANNURONATE ALGINATE COATED TRANSPLANTS, PROCESSES FOR THEIR MANUFACTURE, AND METHODS FOR THEIR USE

[75] Inventors: Randel E. Dorian, Orinda; Kent C. Cochrum, Davis, both of Calif.

[73] Assignees: The Regents of the Univesity of California, Oakland; Metabolex, Inc., Hayward, both of Calif.

[21] Appl. No.: 300,053

[22] Filed: Sep. 2, 1994

Related U.S. Application Data

[62] Division of Ser. No. 891,564, May 29, 1992, Pat. No. 5,429,821.

[51] Int. Cl.$^6$ ............... C12N 11/10; C12N 11/12; C12N 11/08
[52] U.S. Cl. ............... 435/178; 435/177; 435/182; 435/325; 435/382; 424/424
[58] Field of Search ............... 435/240.2, 178, 435/325, 177, 182; 424/424

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,663,286 | 5/1987 | Tsang | 435/178 |
| 4,673,566 | 6/1987 | Goosen et al. | 424/19 |
| 4,689,293 | 8/1987 | Goosen et al. | 435/1 |
| 4,749,620 | 6/1988 | Rha et al. | 428/402.2 |
| 4,803,168 | 2/1989 | Jarvis, Jr. | 435/325 |
| 4,806,355 | 2/1989 | Goosen et al. | 424/424 |
| 5,459,054 | 10/1995 | Skjak-Braek et al. | 435/178 |

FOREIGN PATENT DOCUMENTS 2034641  5/1992  Canada.

*Primary Examiner*—Leon B. Lankford, Jr.
*Attorney, Agent, or Firm*—Hana Verny

[57] ABSTRACT

A transplant with a core of a viable, physiologically active, cell(s) and a non-fibrogenic coating of alkaline earth metal alginate having a high mannuronate to guluronate molar ratio and free from fibrogenic amounts of fucose, sulfate, phloroglucinol and protein moieties. The coating has a permeability sufficiently low and a thickness sufficiently large to protect the tissue cells from host immunological agents after transplantation, the coating also being sufficiently permeable and thin to permit the diffusion of cell sufficient nutrients and cell products through the coating required for cell viability. The alginate coating can be reacted with polylysine to form a polylysine-alginate complex on the outer surface thereof. The complex can then be reacted with polyaspartic acid to provide a physiologically acceptable negative surface charge.

13 Claims, 1 Drawing Sheet

NON-FIBROGENIC HIGH MANNURONATE ALGINATE COATED TRANSPLANTS, PROCESSES FOR THEIR MANUFACTURE, AND METHODS FOR THEIR USE

This is a divisional of application Ser. No. 07/891,564, filed on May 29, 1992 now U.S. Pat. No. 5,429,821.

FIELD OF THE INVENTION

This invention is directed to the field of medical transplants of cells and tissues, the manufacture of such transplants, and their use. In particular, this invention is directed to the coating of such transplants with a novel, highly protective coating of a high polymannuronate alginate free of transplantation impairing amounts of impurities, the coated tissues formed therewith, and to transplantations made using these products.

BACKGROUND OF THE INVENTION AND PRIOR ART

Traditional medical treatments for functional deficiencies of secretory and other biological organs have focused on replacing identified normal products of the deficient organ with natural or synthetic pharmaceutical compositions. For example, for treating insulin-dependent diabetes mellitus, also known as type I or juvenile onset diabetes, the normal secretion of insulin by the islets of Langerhans in the pancreas must be replaced since functional islets are no longer present in the pancreas. This pancreatic function is emulated by administering insulin, titrating the injections in response to blood glucose level measurements. At best, the normal production of the islets are poorly approximated.

Organ replacement has also been applied. This has generally required continuous use of immunosuppressive agents to prevent immunological rejection of the organ, depriving the patient of the full protective function of the immune system against diseases. It has provided permanent relief only for a limited group of organs.

Attempts to transplant organ tissues into genetically dissimilar hosts without immunosuppression have been generally defeated by the immune system of the host. Prior to this invention, application of effective protective barrier coatings to isolate the transplant tissues from the host immune system has not proven to be medically practical for a number of reasons. The coating materials were incompatible with the host system or unsuitable for other reasons. Encapsulation or coating processes previously developed did not yield reproducible coatings having the desired porosity and thickness required for the transplant tissue to have a long and effective functioning life in the host.

To protect transplants from destruction by the immune response of the host animal, various attempts have been made to create a protective barrier between the transplant tissue or cells and the immunological components of the host's system. T. M. S. Chang, Science 146:524–525 (1964) described the microencapsulation of erythrocyte hemolysate and urease in semi-permeable polyamide membranes. These microcapsules did not survive for long when injected into the blood stream. K. Mosbach et al, Acta Chem. Scand. 20:2807–2812 (1966) and T. M. S. Chang et al, Can. J. Physiol. and Pharmacol. 44:115–128 (1966) describe the preparation of semi-permeable microencapsulated microbial cells and viable red blood cells, the latter article mentioning the possibility of using injections of encapsulated cells for organ replacement therapy.

Viable tissue and cells have been immobilized in alginate droplets coated with polylysine by F. Lim et al, J. Pharm. Sci. 70:351–354 (1981), and their attempted use to correct the diabetic state of diabetic animals was reported by Lim et al, Science 210:908–909 (1981). U.S. Pat. Nos. 4,251,387, 4,324,683, 4,352,883, 4,407,957, 4,663,286, and 4,803,168 relate to this research. The products have not been successful for the long term correction of the diabetic state of animals, and they have not proven suitable for transplanting tissues such as pancreatic islets in humans.

Substantial additional efforts to develop transplants encapsulated in calcium alginate droplets reacted with polylysine by M. F. A. Goosen and his associates are reported in their U.S. Pat. Nos. 4,673,566, 4,689,293, 4,789,550, 4,806, 355, 4,789,550, for example. These efforts also have not proven successful in providing protected transplants suitable for transplantation.

Lim et al, Diabetes 40:1511–1516 report the prolonged reversal of the diabetic state of NOD mice with xenografts of microencapsulated rat islets, using alginate-polylysine capsules.

U.S. Pat. No. 4,744,933 describes encapsulating solutions containing biologically active materials in an outer membrane of inter-reacted alginate and polyamino acid.

U.S. Pat. No. 4,696,286 describes a method for coating transplants suitable for transplantation into genetically dissimilar individuals by coating the transplant with a surface-conforming bonding bridge of a multifunctional material that binds chemically to a surface component of the transplant followed by a semipermeable, biologically compatible layer of a polymer that binds chemically to the bonding bridge layer.

Hackel et al, J. Appl. Microbiol. 1:291–296 (1975) and M. Kerstan et al, Biotechnology and Bioengineering 19:387–397 (1977) report the use of calcium alginates for immobilization of microbial cells and enzymes. Nigam et al, Biotechnology Techniques 2:271–276 (1988) and publications cited therein describe methods for coating living cells in an outer membrane of calcium alginate by dropping a calcium solution into an alginate solution and further incubating the capsules in a calcium solution.

Plunkett et al, Laboratory Investigation 90:6204–6205 (1990) describe an angiogenesis model using tumor cells entrapped in alginate beads. A spray of sodium alginate-cell solution droplets was contacted with aqueous calcium chloride solution to form calcium alginate beads. Pump speed and air pressure were used to control the droplet size in the spraying process.

SUMMARY OF THE INVENTION

One aspect of this invention is a novel, alginate fraction having a high polymannuronate content which is non-fibrogenic. It is free from substances which will impair the transplantability of transplants coated with calcium alginate gel products thereof. The compositions of alginates and methods for purifying and fractionating alginates are described by Haug, A., COMPOSITION AND PROPERTIES OF ALGINATES: REPORT NO. 30. Norsk institutt for tang- og tareforskning (Norwegian Institute of Seaweed Research) (1964), Haug, A. Acta Chem. Scand. 13:601–603 (1959); Haug et al, Acta Chem. Scand. 19:1221–1226 (1965); Haug et al, Acta Chem. Scand. 21:691–704 (1967); Smidrød et al, Acta Chem. Scand. 22:1989–1997 (1968); and Skjaak-Bræk et al, Biotechnology and Bioengineering 33:90–94 (1989). Correlations between chemical and physical properties of alginate gel beads has been reported by Martinsen et al, Biotechnology and Engineering. 33:70–89 (1989).

Calcium alginate coated implants have not been previously considered suitable for use in transplanting tissues because the coated transplants did not survive in the host systems. Alginates in the form obtained from seaweeds are primarily mixed polymers of guluronate and mannuronate containing various levels of other materials. Calcium alginate gelation is primarily caused by calcium ion bonding with the guluronic acid moieties of the polymer. High guluronate polymers were selected for coating based on the premise that higher levels of cross-linkage were required to provide a strong protective barrier for transplants.

We have discovered that these earlier failures were the result of several factors. We have found that certain natural materials which are present in commercially available alginate preparations are fibrogenic to the host tissue surrounding the transplant, leading to encapsulation of the transplant in an impervious, poorly vascularized layer of scar tissue, causing transplant necrosis and disfunction. We found that prior art attempts failed to remove substances containing fucose, sulfate, phloroglucinol and protein levels from the alginates to the levels required to avoid fibrosis. Although claims of insulin production from transplanted pancreatic cells were made, inspections of transplanted coated cells always revealed the presence of significant fibrosis. Transplanted cells coated with the purified alginates of this invention did not generate fibrosis.

We have also discovered that the high polyguluronate alginates have large pore structures which did not effectively exclude destructive levels of host immunological agents from the transplants. Alginate coatings having a thickness greater than 200 μm have been reported to lack the permeability required for flow of nutrients and cell products through the coating in amounts sufficient for long term viability of the coated transplant in the host system by Chickeportiche et al, Hormone and Metabolism Research Supplement 26:209–213 (1990). We have developed efficient procedures for mass production of transplants having coatings of alginates with a high mannuronate to guluronate molar ratio and a thickness of less than 200 μm, and we have found that they can be used to restore islet function indefinitely after transplantation.

Prior to this invention, reacting the outer surface of alginate coatings with polylysine was reported to be necessary for alginate coated transplants. We have developed fully operable non-fibrogenic coatings with perfected permeabilities which do not require a secondary reaction of the outer coating with polylysine.

It is one object of this invention to provide a transplant core of coated viable, physiologically active, tissue cells for transplantation which is physiologically acceptable to the host and which effectively provides prolonged protection of the tissue cells, after transplantation, from destruction by the host immune system.

It is another object of this invention to provide a core of such tissue cells enclosed in a coating having a thickness permitting diffusion to the transplants of the amounts of nutrients and other substances required for the health, long life and effective function after transplantation and a permeability allowing effective diffusion and release of transplanted tissue products into the host system.

It is a still further object of this invention to provide an effective transplant coating material which is physiologically acceptable, non-fibrogenic and non-toxic to host tissue and which can be used to provide a coating having the characteristics described above.

It is yet another object of this invention to provide a manufacturing process for effectively coating a transplant (e.g., tissues and other biological substances) with a complete barrier coating which is physiologically acceptable, non-fibrogenic and non-toxic to host tissue and which provides a complete barrier coating with a controlled thickness and permeability to intermediately size proteins.

In summary, this invention comprises a transplant core of coated, viable, physiologically active, tissue cells having a non-fibrogenic coating of alkaline earth metal alginate comprising calcium alginate, magnesium alginate, and mixtures thereof. The coating is free from fibrogenic concentrations of fucose, sulfate, phloroglucinol and protein moieties, which means that any amount in the coating of fucose moieties is less than 1 wt. %, of sulfate moieties is less then 0.5 wt. %, and of phloroglucinol moieties is less than 0.01 wt. %.

Preferably, the alkaline earth metal alginate is formed from an alginate having a mannuronate to guluronate molar ratio of from 1.2 to 6. The coating should have a permeability sufficiently low and a thickness sufficiently large to protect the transplant from recipient or host immunological agents after transplantation, the coating also being sufficiently permeable and thin to permit the diffusion of sufficient cell nutrients and cell products through the coating required for cell viability. Preferably, the coating has a thickness between at least about 20 μm and about 200 μm.

Suitable transplants include, for example, pancreatic islet cells, neural cells, renal cortex cells, vascular endothelial cells, thyroid cells, adrenal cells, thymic cells, ovarian cells or hepatic cells, tissues and the like.

The alkaline earth metal alginate coating can be reacted with a polyamino acid such as polylysine to form a polylysine-alginate complex on the outer surface thereof. The complex can be reacted with a polyamino acid such as polyaspartic acid to provide a physiologically acceptable negative surface charge on the outer surface of the coated tissue cells. Alternatively, the complex coated cells can be reacted with a calcium sequestering agent to at least partially liquify the alginate gel, allowing liquified alginates to diffuse through the polylysine-alginate complex and react with available surface sites of the polylysine, thereby providing the coated cells with a physiologically acceptable negative surface charge on the outer surface thereof. The cells can also be pretreated with polylysine prior to the application of alginate coating thereto.

The process of this invention for making a transplant core of coated, viable, physiologically active, tissue donor cells having a non-fibrogenic coating for transplantation into an immunologically incompatible host comprising the steps of a) coating the tissue cells with an alginate which is free from fibrogenic concentrations of fucose, sulfate, phloroglucinol and protein moieties, and b) reacting the alginate coating with alkaline earth metal cations comprising calcium ions, magnesium ions, or mixtures thereof to form an alkaline earth metal alginate coating.

Preferably, any fucose moieties in the alginate are less than 1 wt. %, any sulfate moieties in the alginate are less then 0.5 wt. %, and any phloroglucinol moieties in the alginate are less than 0.01 wt. %, and the mannuronate to guluronate molar ratio of the alginate is from 1.2 to 6.

DETAILED DESCRIPTION OF THE INVENTION

Figure 1:
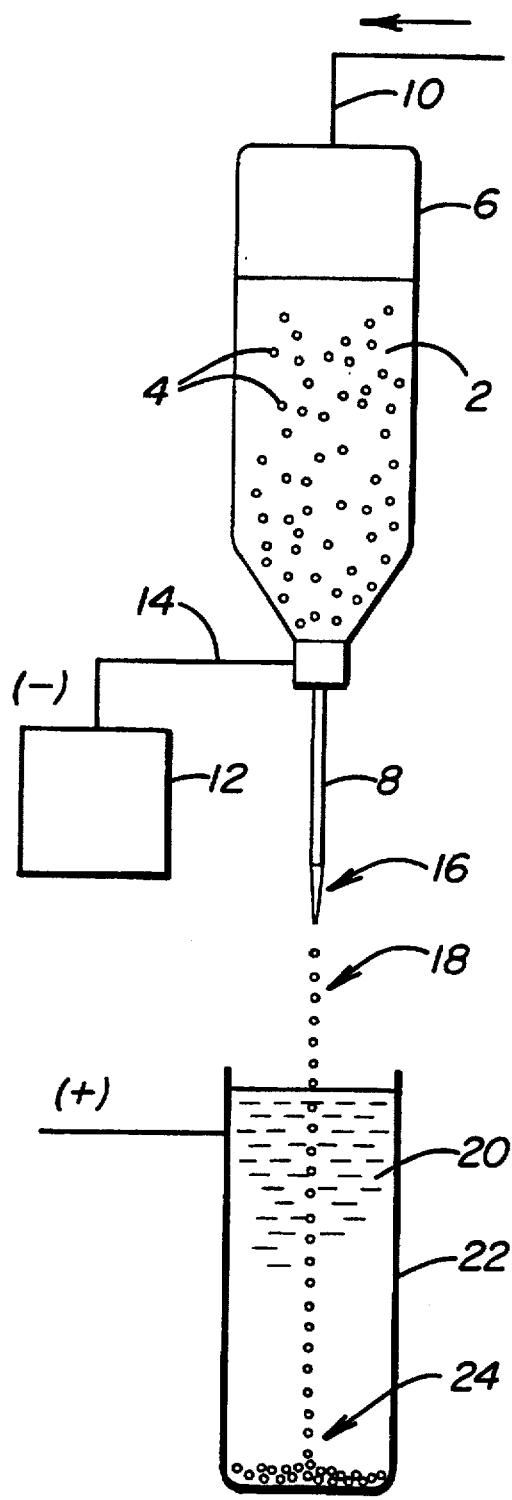
FIG. 1 is a schematic representation of the electrostatic apparatus preferred for use in the process of this invention.

The coated transplant of this invention is effective for implantation into a host animal by simple injection through a hypodermic needle having a needle diameter sufficient to permit passage of a suspension of coated transplant therethrough without damaging the coating.

The term "transplant", as used herein, is defined to include all living tissues, cells, and biologically active substances intended-to be implanted into the body of a host animal and the act of implanting or transferring these tissues and cells from donor to host. These tissues and cells include, without limitation, tissue and cells removed from a donor animal, tissue and cells obtained by incubation or cultivation of donor tissues and cells, cells obtained from viable cell lines, biologically active products of cells and tissues, and the like.

Any type of tissue or cells for which transplantation is desired can be coated and transplanted according to this invention. The most common tissues for transplants are secretory organ tissues, where transplantation from a donor organ to a recipient or host animal is desired to at least partially replicate the donor organ's action in the host system. Preferred donor tissues are pancreatic islets, hepatic cells, neural cells, renal cortex cells, vascular endothelial cells, thyroid cells, adrenal cells, thymic cells and ovarian cells.

The process of this invention is described hereinafter for the preparation and transplantation of pancreatic islets and islet cells by way of example for purposes of clarity of explanation and not by way of limitation. This process can be equally well applied to other organ tissues as will be readily apparent to a person skilled in the art, with conventional and obvious modifications as required to accommodate any uniquely different requirements of the different tissues. Applications of the process to all tissues and cells suitable for transplantation are intended to be within the scope of this invention.

Isolated pancreatic islets (or other cells or tissues suitable for transplantation) are be prepared by conventional procedures to substantially separate them from extraneous tissue and other donor substances.

In a first step of the process of this invention, isolated pancreatic islets (or other cells or tissue) are washed with isotonic saline and suspended in a solution of purified, low molecular weight, mannuronate-enriched heterogeneous polyuronic acid salt. Optionally, the washed cells can be pretreated with an aqueous solution of poly-L-lysine to increase bonding of cells with alginate, followed by rinsing with saline.

The low molecular weight, mannuronate-enriched alginate is selected to provide the low molecular permeability of the calcium alginate gel coating required for a protective barrier excluding immunologically effective concentrations of the host immune system agents from the tissue and the permeability required to permit sufficient diffusion of nutrients and other substances to the transplants required for their long life and viability. This property is the product of the combined effect of three characteristics. First, the selection of a low intrinsic viscosity alginates allows the use of higher concentrations of alginates in the suspending medium. Secondly, selecting alginates having a shorter chain length decreases effective gel permeability. Finally, the calcium reaction product of alginates having a high mannuronate to guluronate molar ratios yields a coating with a low effective permeability.

The viscosity of coating solutions of the alginates having a concentration of from about 0.7 to 2.5 weight percent alginate should have a viscosity of from about 30 to 250 centipoises and preferably from about 50 to 150 centipoises at 25° C.

The alginates should have an average chain length corresponding to a polymer molecular weight of from about 10 to 200 kilodaltons and preferably from about 12 to 80 kilodaltons. Molecular weights and average chain lengths below these ranges yield a calcium alginate gel with a physical strength which is insufficient to provide the integrity required for implantation and long term exclusion of immune system agents.

The mannuronate to guluronate molar ratio of the coating polymer should be from about 1.2 to 6 and is preferably from about 1.5 to 2.5. A mannuronate to guluronate molar ratio above these ranges is undesirable because the coating obtained therewith tends to swell and weaken when placed in the host body, increasing the permeability size and lengthening the nutrient diffusion path through the coating.

Average molecular weight and overall mannuronate to guluronate molar ratios are initially determined substantially by material origin but can be adjusted somewhat by physical and chemical methods. Molecular weights can be reduced, for example, by partial acid hydrolysis, thermal degradation or sonication. High molecular weights can be obtained by controlled precipitation methods with concomitant alteration of alginate composition or by dialysis, molecular filtration, or gel exclusion chromatography. The mannuronate to guluronate ratio can be increased or decreased by selective precipitation or solubilization by mono- and di-valent metal cations, organic solvents or acids. Adjustment of these characteristics may be required to obtain optimum results with different tissue transplants.

The cell suspension in alginate is formed into droplets, and the droplets are contacted with a suitable gelling solution comprising, e.g., alkaline earth metal solution to gel the alginate. The droplets can be formed by any conventional procedure. For example, alginate droplets have been formed by emulsifying a solution of sodium alginate containing cellular material to form droplets of sodium alginate and cells, and gelling the droplets with calcium chloride in U.S. Pat. No. 4,352,883. Alginate droplets have also been formed with a syringe and pump to force droplets from a needle, using a laminar flow air knife to separate droplets from the tip, the droplets being galled by collecting them in a calcium chloride solution in U.S. Pat. No. 4,407,957. Alginate droplets have also been formed by the simple procedure of expelling them from a hypodermic needle and allowing the droplets to fall in to a calcium chloride solution, as described by Nigam et al, *Biotechnology Techniques.* 2:271–276 (1988). Droplets have also been injected into a concurrently flowing stream containing calcium chloride in U.S. Pat. No. 3,962,383. Spraying alginate solutions through a spray nozzle to form a mist of droplets which was collected in a calcium chloride solution was reported by Plunkett et al, *Laboratory Investigation.* 62:510–517 (1990). These methods have not proven effective for mass production of coatings suitable for successful transplantation.

Hommel et al in U.S. Pat. No. 4,789,550 disclosed the formation of alginate droplets using a combination of a needle and a pulsed electrical electrostatic voltage to form uniform droplets. The alginate solution was forced through a needle tip to form a droplet, and the droplet was pulled from the needle by a changing electrostatic field between the needle tip and a calcium chloride solution placed below the needle tip. The droplet received a charge of one polarity from the needle, opposite to the charge in the calcium chloride solution. When the voltage difference between the droplet and the oppositely charged calcium chloride solution reached a threshold value at which the attraction by the solution on the droplet exceeded the force of interfacial tension holding the droplet on the needle tip, the droplet was pulled free to fall into the calcium chloride solution. The electrostatic field was fluctuated using a square wave form to create a succession of voltages crossing the threshold value, thus producing a continuous series of droplets, one per square wave cycle. The process was not found to provide the small droplets and thin coatings required for effective transplantation.

Figure 2:
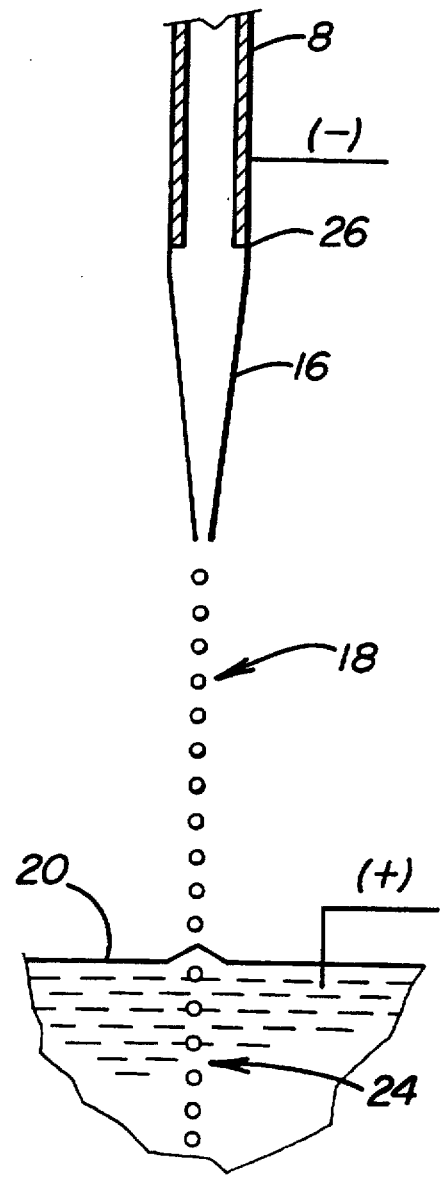
FIG. 2 is an enlarged schematic representation of the liquid stream showing the stream attenuation and drop formation in the electrostatic apparatus of FIG. 1.

The preferred drop forming and gelling procedure is described in copending, concurrently filed patent application Ser. No. 07/890,982 and described hereinafter. FIG. 1 is a schematic representation of the electrostatic apparatus of this invention, and FIG. 2 is an enlarged schematic representation of the liquid stream showing the stream attenuation and drop formation in the electrostatic field created by the apparatus. A coating solution 2 containing electrolytes and suspended transplant tissue fragments or cells 4 is provided in a reservoir 6. An orifice outlet for a thin stream of coating solution is provided by needle 8 communicating with the liquid in the reservoir. Pressure for expelling liquid from the reservoir 6 through the needle 8 can be provided by any conventional system, such a gas pressure supply line 10 or alternatively, a plunger, pump or other conventional system.

An electrostatic voltage is applied to the metal needle 8 or to the solution from a conventional high DC voltage source such as a van de Graaff generator or other conventional high voltage DC power supply 12 through electrical connection 14. The voltage must be constantly at a level sufficient to continuously form an attenuated stream of suspension 16 forming a continuous series of droplets 18 having a constant size. The droplets are collected in a solution 20 contained in droplet collector 22, the solution 20 having a charge opposite to the charge of the needle 8. Solution 20 provides the reagents or conditions required to solidify the droplets, forming the coated transplantation products 24.

In the embodiment shown in FIG. 1, the needle has a negative charge and the an electroconductive collection container 22 has a positive charge. It will be readily apparent to a person skilled in the art that alternative configurations can be provided to yield a high voltage electrostatic potential of opposite charges between the needle 8 and the solution 20. For example, the polarities can be reversed, and the needle 8 can have a positive charge relative to the solution 20.

Without the electrostatic attraction of the solution 20 for the liquid leaving the needle 8, large individual droplets would be formed, their size being determined only by gravitational force, the interfacial tension of the solution and the flow rate, yielding a coating with excessive thickness. We have found that coatings of the desired size can be obtained when the continuous attraction of the solution 20 for the liquid leaving the needle is at least about $1 \times 10^{-6}$ newtons for coating solutions having a viscosity of from about 50 to 150 centipoises. In prior art processes, needle size must be reduced to produce smaller droplets, requiring increased pressures and placing a practical lower limit on the sizes which can be obtained. Since the particle sizes produced by the process of this invention are independent of the needle size, the smallest particles can be produced, even with the largest needles. This permits small particles to be formed from viscous solutions with a minimum of pressure.

For needle orifices 8 having inner diameters of from 0.1 to 2 mm, electrostatic DC voltages of from 1 to 400 KV have been found to be satisfactory for operation in air under ambient conditions. Currents ranging from 0.2 µA to 3.5 µA are suitable.

The process of this invention for coating a biological material such as transplant tissues with a uniformly sized coating of polymer using the apparatus described above comprises dispersing the biological material in an aqueous solution of the polymer 2. Then the aqueous solution is discharged from an orifice 8 in a continuous stream 16 above an alkaline earth metal, preferably calcium ion, liquid 20 capable of gelling the polymer while placing an electrical charge of one polarity on the stream while it is being discharged. An electric charge of opposite polarity is maintained on the liquid 20, the electric charge being sufficient to continuously attenuate the stream of aqueous solution to form a continuous stream of droplets having a reproducible size. The polymer droplets are then gelled to form a continuous polymer coating on the biological material and smoothing the coating to form spherical coated particles by collecting the droplets in the liquid 20. Preferably, the polymer solution has a viscosity of from about 50 to about 150 centipoises, and the orifice has a diameter of from about 0.2 to 0.8 mm.

The alkaline earth metal cation concentration, expressed as calcium chloride, should be at least 0.5 weight percent of the solution 20.

The products of this process are coated transplant cores of viable, physiologically active, tissue cells such as pancreatic islet cells having a coating thickness of from 20 to 200 μm. The coating comprises alkaline earth metal alginate selected from the group consisting of calcium alginate, magnesium alginate, and mixtures thereof, the alkaline earth metal alginate having been formed from an alginate having a mannuronate to guluronate moiety molar ratio of from 1.2 to 6 and being free from impurities which would impair viability and long life of tissue transplants coated with the calcium reaction product thereof. The coating preferably has a permeability sufficiently low and a thickness sufficiently large to protect the tissue cells from host immunological agents after transplantation, the coating also being sufficiently permeable and thin to permit the diffusion of cell nutrients and cell products through the coating sufficient for cell viability. The coating preferably a thickness of at least about 20 μm and less than about 200 μm.

If further reduction of molecular permeability is desired or reduction of swelling of alginate coating is required, the calcium alginate gel coating can be cross-linked with poly-L-Lysine or other physiologically acceptable, non-toxic polycation by immersing the coated tissue in a solution of the polycation polymer. The reduction in permeability is a function of the degree of polymerization of the polycation, reaction of the polycation with the alginate coating, concentration of the polycation in solution and the incubation time. The selection of the optimum polycation and reaction conditions is conventional and fully within the skill of the art. The reaction is terminated by depletion of the polymer from the solution or by dilution of washing.

Polylysine, and polycations in general, induce fibrosis and a further treatment of the alginate-polycation complex is desirable to improve biocompatibility of the coated product.

Immersion of the polycation reacted products in a solution of sodium alginate to react free epsilon-amino groups at the coating surface leads to an ion exchange reaction in which the calcium alginate core is partially or completely solubilized by depletion of the alkaline earth metal cations therefrom. However, if trace amounts of soluble alginate remain after such treatment, slow diffusion of the liquified materials from the capsule can lead to a fibrotic reaction, particularly when the alginate is known to induce fibrosis in its soluble form. If the alginate treated products are treated with calcium ion before complete solubilization of the alginates and their removal from the core, the calcium ion reacts with the sodium alginate migrating outward across the coating layer, compromising membrane distinctness and increasing the likelihood of fibroblastic adhesion to the coating surface.

Therefore, if alginate is to be used in the outer coating, the reaction should be carried out to completely dissolve the core gel either by ion exchange or chelation of the calcium ion, for example with sodium citrate or EDTA. The product is then washed exhaustively with several changes of wash medium or by percolation, allowing ample time for the soluble alginate to diffuse entirely out of the coating. As alginate diffuses outward through the coating, residual free amino groups of the polycation react therewith.

Preferably, a negative charge is applied to the polycation complexed alginate coated tissue transplants by reacting them with polyaspartic acid. Because of its lower binding affinity, it is less likely to complex and deplete calcium from the primary alginate gel coating. It reacts with the polycation without dissolution of the primary alginate coating. Use of polyaspartic acid as the final reactant provides several advantages over the use of an alginate final complex. It provides greater mechanical strength, smaller resultant coated product diameter, and low permeability because of the additional cross-linking and reduction of the volume of the condensed coating.

This invention is further illustrated by the following specific but non-limiting examples. Percents are given in weight percents and temperature in degrees Centigrade unless otherwise specified.

EXAMPLE 1

Sodium Alginate Preparation

Low viscosity sodium alginate (LV Alginate, KELCO DIV. of Merck & Co.) isolated from *Macrocystis purifera* was dissolved in a neutral solution of HEPES buffered saline, clarified by centrifugation, and filtered to remove particulates. The solution was passed through perchlorate-bleached activated charcoal (Mallinckrodt activated charcoal powder) to remove organic contaminants such as polyphenols. The resulting clear solution was precipitated by adding sufficient 1N HCl to reduce the solution pH to 2. The precipitate was pelleted by centrifugation and redissolved in aqueous sodium chloride solution containing sufficient EDTA (about 2 ppm) to chelate any trace calcium and magnesium ions which were present in the sodium chloride reagent. The solution was reprecipitated by adding ethanol, and the precipitate was separated from the solution and redissolved in a 1M solution of potassium chloride to redissolve the guluronate-rich fraction. The insoluble material remaining was pelleted by centrifugation, redissolved in aqueous NaCl solution containing sufficient EDTA (about 2 ppm) to chelate any trace calcium and magnesium ions which were present in the sodium chloride reagent, and reprecipitated with ethanol. The precipitate was collected on a fine mesh sieve, and the remaining salt and trace organic impurities were washed from the precipitate with copious volumes of aqueous solutions of ethanol with NaCl (with EDTA) of sequentially increasing proportions of alcohol and decreasing salt concentration. The material was finally washed in absolute ethanol, the excess alcohol removed, and the material was fluffed and dried at 80° C. in a circulating oven.

The resulting dry material was dissolved in HEPES-buffered dilute sodium citrate, 0.01M, with NaCl added to isoosmolarity and filtered through a 0.1 micron membrane.

EXAMPLE 2

Pancreatic Suspension Islet Preparation

Pancreatic islets isolated from rat were washed with isotonic saline, were suspended in an alginate solution prepared by dissolving the alginate prepared by the procedure of Example 1 at a concentration of 10,000 islets per ml in 1.9 wt. % purified alginate in 10 mM HEPES, 0.01M sodium citrate, containing sufficient sodium chloride required for isoosmolarity (about 0.81 wt. %), the final solution having a viscosity of about 50 centipoises at 32° C. The islets had an approximate average diameter of 150 µm.

This procedure was repeated with dog islets.

EXAMPLE 3

Pancreatic Islet Coating

Using a DC electrostatic voltage of 8 KV provided by a van de Graaff generator between needle tip and grounded 0.117M aqueous calcium chloride solution at ambient temperature, a suspension of pancreatic islets (25 islets per µL) prepared by the procedure of Example 2 was passed through a 20 gauge needle at a flow rate of approximately 200 µl/min. The suspension emerged from the needle as a thin, attenuated stream which transformed into droplets, the droplets being collected in the calcium chloride solution. The droplets were gelled by reaction with the calcium ion in the solution. The calcium alginate coatings on the islets were smooth and uniform and had an approximate thickness of about 130 µm. The total coated particle had an average diameter of about 360 µm.

This process was repeated with dog islets prepared by the procedure of Example 2.

EXAMPLE 4

Pancreatic Islet Transplant into Diabetic Mice (IP)

Host Balb/C mice were rendered diabetic by IP injection of streptozocin (250 mg/kg) at 50 mg/mL in 0.1M citrate buffer, pH 4.5 several days prior to transplant.

Coated dog islets prepared by the procedure of Example 3 were injected IP, 2000–3000 islets per mouse, into one group of mice. The mice became and have remained euglycemic as of the filing date hereof.

Spheres formed from the same alginate (without cells) were injected IP into a control group of Balb/C mice. The mice were sacrificed weekly for up to 16 weeks. The alginate spheres were examined histologically and found to be free from fibrosis and macrophages.

EXAMPLE 5

Pancreatic Islet Transplant into Diabetic Dog

A dog's spleen was injected via the splenic vein using a 16 gauge needle with coated dog islets prepared by the procedure of Example 3. The coated islets were suspended in saline, 10 mM HEPES, containing 10 mM $Ca^{++}$ ions at a density of 1300 coated islets per mL of injection volume.

Three weeks after transplantation, the dog was anesthetized, and the splenic artery and vein were cannulated to determine if the coated islets in the spleen were producing insulin. The dog received a dextrose bolus (5 mg/Kg) via a tributary of the splenic artery to stimulate insulin release from the coated islets in the spleen. Blood samples were taken from the splenic artery and vein 10 min prior to the bolus injection and at 2 min intervals following the dextrose injection.

Insulin was detected in the splenic vein following the dextrose challenge (14–40 uIU/mL). Before the dextrose challenge, the splenic vein insulin levels were baseline (2–2.5 uIU/mL).

Histology of the coated islets in the spleen demonstrated viable islets with no associated fibrosis or macrophages. These results indicate that the coating protected the transplanted islets and that the islets had an insulin response following a dextrose challenge.

The invention claimed is:

1. A process of making a transplant coated with a non-fibrogenic coating, said process comprising steps:
   (a) coating a transplant core with a high mannuronate low guluronate alginate free from fibrogenic concentrations of fucose, sulfate, phloroglucinol and protein moieties; and
   (b) reacting the alginate coating with alkaline earth metal cations to form an alkaline earth metal alginate coating.

2. The process of claim 1 wherein an alkaline earth metal cation is selected from the group consisting of calcium ions, magnesium ions, and a mixture thereof.

3. The process of claim 2 wherein, in step (a), the concentration of fucose moieties is less than 1 wt. %, the concentration of sulfate moieties is less than 0.5 wt. %, and the concentration of phloroglucinol moieties is less than 0.01 wt %.

4. The process of claim 3 wherein the high mannuronate alginate has a mannuronate to guluronate molar ratio of from 1.2:1 to 6:1.

5. The process of claim 4 wherein the alkaline earth metal cation is calcium.

6. The process of claim 5 wherein the alginate coating has a permeability sufficiently low and a thickness sufficiently large to protect the tissue cells from host immunological agents after transplantation, the coating being sufficiently permeable and thin to permit a diffusion of cell nutrients into the transplant and a transport of cell products from the transplant through the coating, said diffusion of nutrients and transport of cell products sufficient for cell viability.

7. The process of claim 6 wherein the coating has a thickness between about 20 μm and about 200 μm.

8. The process of claim 7 wherein the transplant core is selected from the group consisting of pancreatic islet cells, neural cells, renal cortex cells, vascular endothelial cells, thyroid cells, adrenal cells, thymic cells, ovarian cells, and hepatic cells.

9. The process of claim 8 wherein the transplant core are pancreatic islet cells.

10. The process of claim 1 further comprising step:
    (c) reacting the alkaline earth metal alginate coating with an aqueous solution containing sufficient polylysine to form a polylysine-alginate complex on the outer surface of said coatings.

11. The process of claim 10 further comprising step:
    (d) reacting the polylysine-alginate complex with an amount of polyaspartic acid sufficient to negatively charge the coating.

12. The process of claim 10 further comprising step:
    (e) reacting the polylysine-alginate complex coating with an alkaline earth metal sequestering agent to at least partially liquify the alginate, wherein liquified alginate reacts with available reaction sites of the polylysine, thereby negatively charging the coating.

13. The process of claim 1 further comprising a pretreatment step of contacting said transplant material with polylysine prior to step (a).

* * * * *

UNITED STATES PATENT AND TRADEMARK OFFICE
CERTIFICATE OF CORRECTION

PATENT NO. : 5,693,514
DATED : December 2, 1997
INVENTOR(S) : Randel E. Dorian, Kent C. Cochrum, Susan A. Jemtrud It is certified that error appears in the above-identified patent and that said Letters Patent is hereby corrected as shown below:

Title page, item [75]
Please add -- Susan A. Jemtrud, San Francisco, California -- as a co-inventor; and change "both" to --all--.

Signed and Sealed this

Fourteenth Day of November, 2000

Attest:

Q. TODD DICKINSON

Attesting Officer

Director of Patents and Trademarks